(12) United States Patent
Lee

(10) Patent No.: US 10,197,535 B2
(45) Date of Patent: Feb. 5, 2019

(54) APPARATUS AND METHOD FOR FULL-FIELD PULSE-ECHO LASER ULTRASONIC PROPAGATION IMAGING

(71) Applicant: KOREA ADVANCED INSTITUTE OF SCIENCE AND TECHNOLOGY, Daejeon (KR)

(72) Inventor: Jung Ryul Lee, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 72 days.

(21) Appl. No.: 15/007,413

(22) Filed: Jan. 27, 2016

(65) Prior Publication Data

US 2016/0349217 A1 Dec. 1, 2016

(30) Foreign Application Priority Data

May 29, 2015 (KR) .................. 10-2015-0075834

(51) Int. Cl.
*G01N 29/24* (2006.01)
*G01N 29/06* (2006.01)
*G01N 29/04* (2006.01)

(52) U.S. Cl.
CPC ....... *G01N 29/069* (2013.01); *G01N 29/2418* (2013.01)

(58) Field of Classification Search
CPC ...... G01N 29/04; G01N 29/06; G01N 29/069; G01N 29/24; G01N 29/2418
USPC ................... 73/643, 633, 621, 634
See application file for complete search history.

(56) References Cited

U.S. PATENT DOCUMENTS 7,100,449 B2 * 9/2006 Busch .................. G01N 29/223
73/618

FOREIGN PATENT DOCUMENTS

| JP | 2001-156425 A | 6/2001 |
| KR | 2007-0033062 A | 3/2007 |
| KR | 2007-0077251 A | 7/2007 |
| KR | 10-2010-0032676 A | 3/2010 |
| KR | 2011-0098301 A | 9/2011 |

* cited by examiner

*Primary Examiner* — Manish S Shah
*Assistant Examiner* — Suman K Nath
(74) *Attorney, Agent, or Firm* — Sughrue Mion, PLLC

(57) ABSTRACT

A system and method for full-field pulse-echo laser ultrasonic propagation imaging is provided. The full-field ultrasonic propagation imaging system generates ultrasounds on a structure by scanning the structure and emitting laser beams, simultaneously senses ultrasounds propagated through thickness of the structure, and generates a through-the-thickness ultrasonic propagation image. Accordingly, the full-field pulse-echo laser ultrasonic propagation imaging can visualize information on through-the-thickness defects in a full field.

7 Claims, 7 Drawing Sheets

APPARATUS AND METHOD FOR FULL-FIELD PULSE-ECHO LASER ULTRASONIC PROPAGATION IMAGING

CROSS-REFERENCE TO RELATED APPLICATION(S) AND CLAIM OF PRIORITY

The present application claims the benefit under 35 U.S.C. § 119(a) to a Korean patent application filed in the Korean Intellectual Property Office on May 29, 2015, and assigned Serial No. 10-2015-0075834, the entire disclosure of which is hereby incorporated by reference.

TECHNICAL FIELD OF THE INVENTION

The present invention relates generally to an apparatus and method for imaging, and more particularly, to an apparatus and method for laser ultrasonic propagation imaging.

BACKGROUND OF THE INVENTION

C-scan, which is one of the results based on an ultrasonic testing (UT) technique from among techniques of detecting defects in structures, shows an excellent result in detecting defects in structures, and thus is being used in many industrial fields. However, the conventional ultrasonic testing technique requires much time as it uses couplant and a contact transducer. In addition, in recent years, noncontact ultrasonic testing is conducted through an air-coupled transducer, but an inspection distance is a few centimeters and thus there is a limit to the inspection.

Recently, a method which generates ultrasounds of a wideband on a surface of a structure through a laser ultrasonic generator of a thermoeleastic mechanism, and uses ultrasounds generated in the structure is actively studied and researched.

Since the current researches and techniques use a single point as an ultrasound source and utilize ultrasounds propagated in an in-plane direction, an in-plane damage or defect is not exactly detected, and also, information on through-the-thickness defects is not provided.

Therefore, there is a need for a method for visualizing information of through-the-thickness defects in a full field.

SUMMARY OF THE INVENTION

To address the above-discussed deficiencies of the prior art, it is a primary aspect of the present invention to provide an apparatus and method for full-field pulse-echo laser ultrasonic propagation imaging, which can visualize information on through-the-thickness defects in a full field.

According to one aspect of the present invention, a full-field ultrasonic propagation imaging system includes: a generator configured to generate ultrasounds on a structure in a noncontact method by emitting laser beams; a receiver configured to sense ultrasounds propagated through thickness of the structure in a noncontact method; and an image generating device configured to generate an ultrasonic propagation image using results of generating ultrasounds by scanning the structure with the generator and the receiver simultaneously, and results of sensing.

A point at which the ultrasounds are generated and a point at which the ultrasounds are sensed may be the same or adjacent to each other.

The receiver may be configured to receive the laser ultrasounds in the noncontact method.

The ultrasound propagation image may be an image which shows a process of propagating the ultrasounds through the thickness of the structure with time.

The ultrasound propagation image is a moving image or an image in which results of sensing acquired through scanning are arrayed in a time domain.

The ultrasound propagation image is a moving image or an image in which results of sensing acquired through scanning are arrayed in a frequency, wave number, or wavelength domain.

The full-field ultrasonic propagation imaging system may further include a controller configured to, when a signal-to-noise ratio is less than or equal to a reference, control the generator and the receiver to scan the structure repeatedly.

The full-field ultrasonic propagation imaging system may further include: a filter mirror configured to pass laser beams emitted from the generator therethrough and transmit the laser beams to the structure, and reflect sensing laser beams reflected from a reflection mirror and transmit the sensing laser beams to the structure; and the reflection mirror configured to reflect the sensing laser beams generated in the receiver to the filter mirror.

The generator may be configured to emit Q-switched laser beams and generate ultrasounds on the structure.

The receiver may be configured to sense the ultrasounds propagated to a continuous wave laser interferometer.

The system may be configured to scan one surface of the structure with the generator and the receiver and generate and sense ultrasounds.

According to another aspect of the present invention, an ultrasonic propagation imaging method includes: generating ultrasounds on a structure by emitting laser beams; sensing ultrasounds propagated through thickness of the structure; and generating an ultrasonic propagation image using results of the generating and the sensing by scanning the structure.

According to another aspect of the present invention, a full-field ultrasonic propagation imaging system includes: a generator configured to generate ultrasounds on a structure by emitting laser beams; a receiver configured to sense ultrasounds propagated through thickness of the structure; and an image generating device configured to generate an ultrasonic propagation image using results of sensing of the receiver, and a point at which the ultrasounds are generated by the generator and a point at which the ultrasounds are sensed by the receiver may be the same as or adjacent to each other.

According to exemplary embodiments of the present disclosure as described above, the full-field pulse-echo laser ultrasonic propagation imaging can visualize information on through-the-thickness defects in a full field.

In particular, according to exemplary embodiments of the present disclosure, a broad ultrasonic field is created as much as a scan area by scanning with ultrasound generation laser beams and sensing laser beams simultaneously, and signals coming back as the ultrasonic field is propagated through the thickness are configured in a time domain, a frequency domain, a wave number domain, or a wavelength domain through a 3-dimensional ultrasonic propagation imaging technique, so that defects or damages on a structure can be visualized with high accuracy and sensitivity.

In addition, when a signal-to-noise ratio is low, the full-field ultrasonic propagation imaging system according to an exemplary embodiment of the present disclosure can continuously increase the signal-to-noise ratio through repeated scanning, and can successfully visualize defects even in a structure which is thick and is easy to attenuate, and can provide the location of a through-the-thickness damage or defect even when the damage or defect is accessed only from one side.

Other aspects, advantages, and salient features of the invention will become apparent to those skilled in the art from the following detailed description, which, taken in conjunction with the annexed drawings, discloses exemplary embodiments of the invention.

Before undertaking the DETAILED DESCRIPTION OF THE INVENTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION OF THE INVENTION

Figure 1:
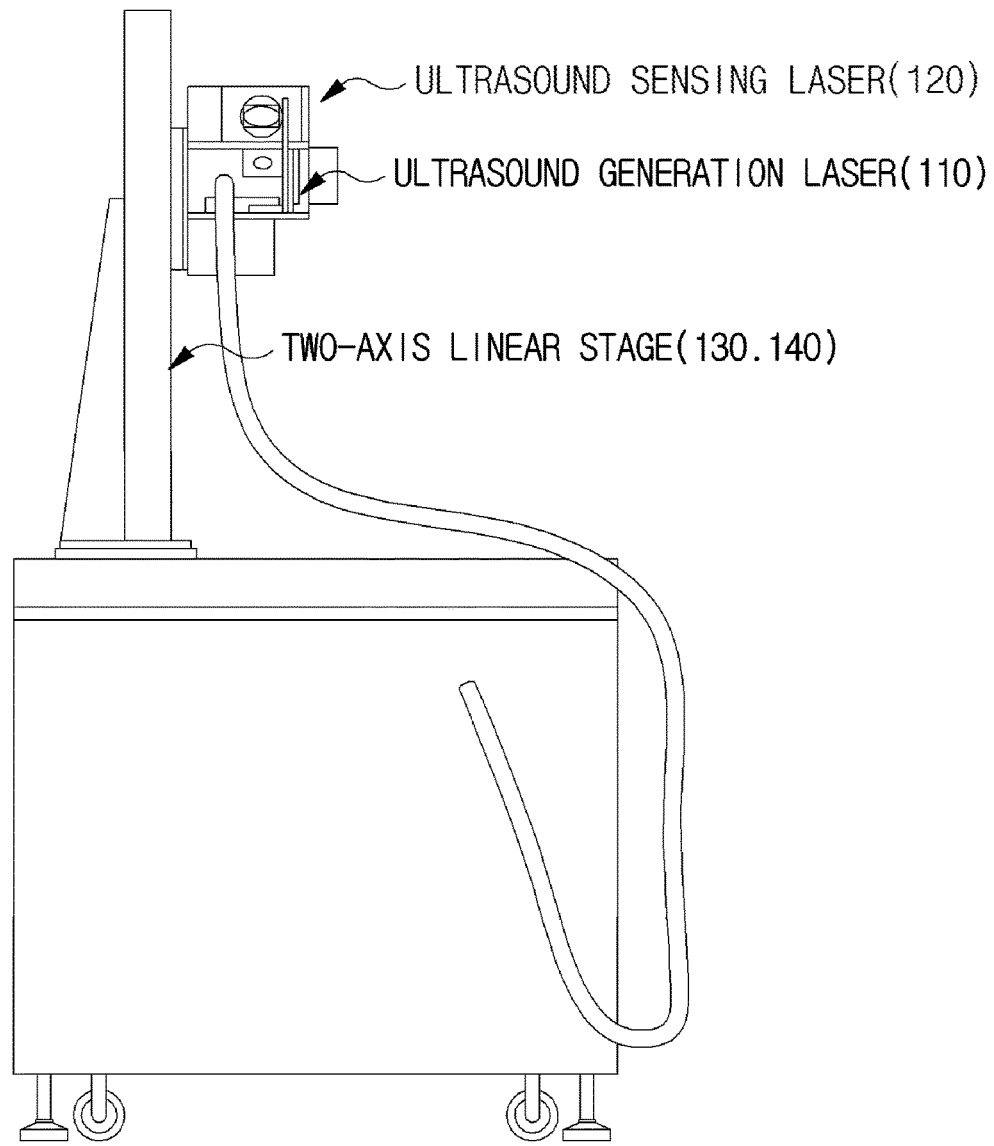
FIG. 1 is a view showing an exterior of a full-field pulse-echo laser ultrasonic propagation imaging system according to an exemplary embodiment of the present disclosure.

Reference will now be made in detail to the embodiment of the present general inventive concept, examples of which are illustrated in the accompanying drawings, wherein like reference numerals refer to the like elements throughout. The embodiment is described below in order to explain the present general inventive concept by referring to the drawings.

FIG. 1 is a view showing an exterior of a full-field pulse-echo laser ultrasonic propagation imaging system according to an exemplary embodiment of the present disclosure.

In the "full-field pulse-echo laser ultrasonic propagation imaging system" (hereinafter, referred to as a "full-field ultrasonic propagation imaging system") according to an exemplary embodiment of the present disclosure, an ultrasound generation point formed through a laser ultrasonic generator is the same as or adjacent to an ultrasound sensing point formed through a noncontact laser ultrasonic receiver, and the full-field ultrasonic propagation imaging system collects through-the-thickness ultrasounds.

In addition, the full-field ultrasonic propagation imaging system according to an exemplary embodiment of the present disclosure scans one surface of a structure with ultrasound generation laser beams and sensing laser beams for generating ultrasounds simultaneously, and creates an ultrasonic field as large as a scan area. Then, signals coming back as the ultrasonic field is propagated through the thickness of the structure are configured through a three-dimensional ultrasonic propagation imaging technique, and thus can visualize defects and damages of the structure with high accuracy and sensitivity.

In addition, when a signal-to-noise ratio is low, the full-field ultrasonic propagation imaging system according to an exemplary embodiment of the present disclosure can continuously increase the signal-to-noise ratio through repeated scanning, and can successfully visualize defects even in a structure which is thick and is easy to attenuate, and can provide the location of a through-the-thickness damage or defect.

Figure 2:
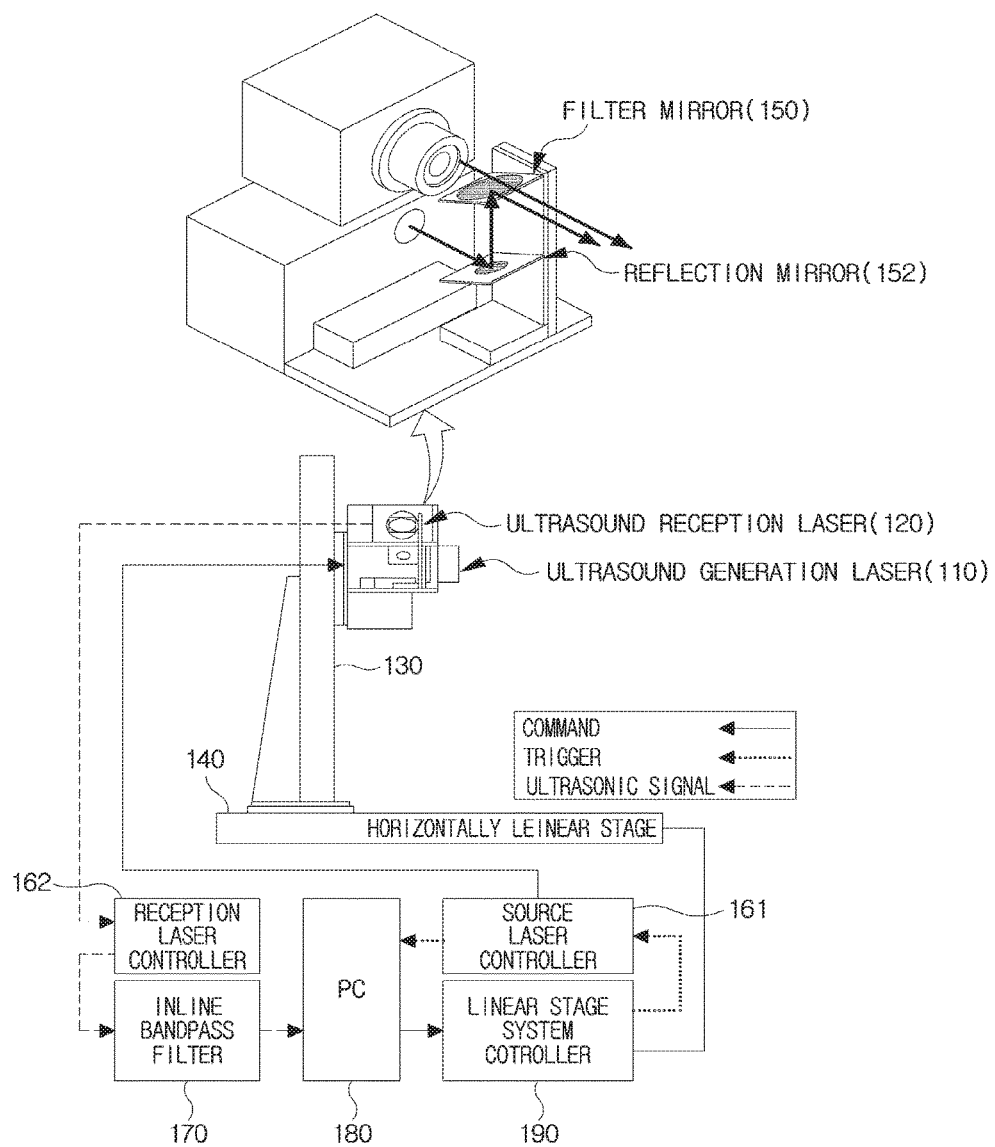
FIG. 2 is a view showing a detailed configuration of the full-field ultrasonic propagation imaging system shown in FIG. 1.

FIG. 2 illustrates a detailed structure of the full-field ultrasonic propagation imaging system shown in FIG. 1. As shown in FIG. 2, the full-field ultrasonic propagation imaging system according to an exemplary embodiment of the present disclosure includes an ultrasound generation laser 110, an ultrasound sensing laser 120, a vertically linear stage 130, a horizontally linear stage 140, a filter mirror 151, a reflection mirror 152, a source laser controller 161, a sensing laser controller 162, an inline band pass filter 170, a PC 180, and a linear stage system controller 190.

The ultrasound generation laser 110 is a laser ultrasonic generator which generates ultrasounds on a structure by emitting source laser beams. The ultrasound generation laser 110 may be implemented by using a Q-switched laser. The ultrasound generation laser 110 is controlled by the source laser controller 161.

The ultrasound sensing laser 120 is a noncontact laser ultrasonic receiver which senses ultrasounds propagated through the thickness of the structure using a Laser Doppler Vibrometer (LDV). The ultrasound sensing laser 120 may be implemented by using a continuous wave laser interferometer, an LDV sensor, etc. The ultrasound sensing laser 120 may be controlled by the sensing laser controller 162.

The source laser beams generated in the ultrasound generation laser 110 passes through the filter mirror 151 and is emitted toward the structure. The sensing laser beams generated in the ultrasound sensing laser 120 are reflected on the reflection mirror 152 and the filter mirror 151 and transmitted to the structure, and are sensed through a reverse path.

Figure 3A:
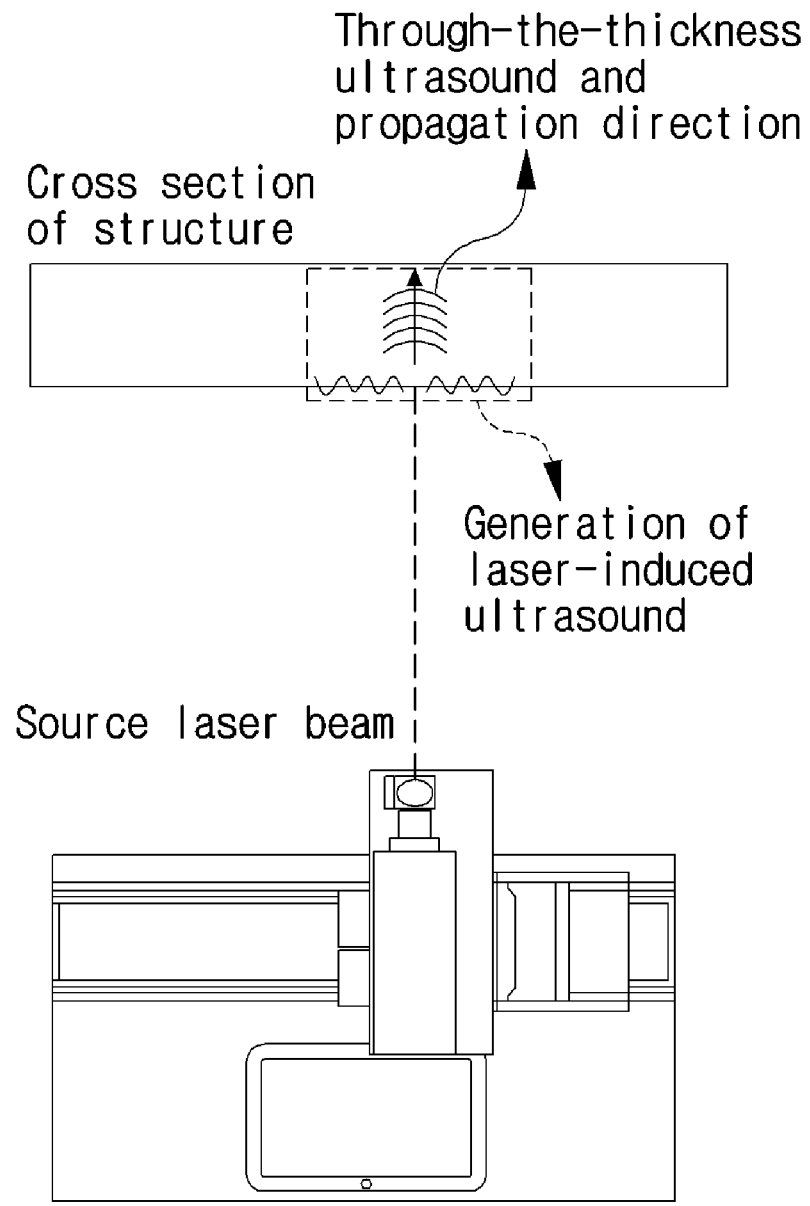
FIGS. 3A and 3B are a view showing a concept of collection in a through-the-thickness ultrasonic propagation mode.
Figure 3B:
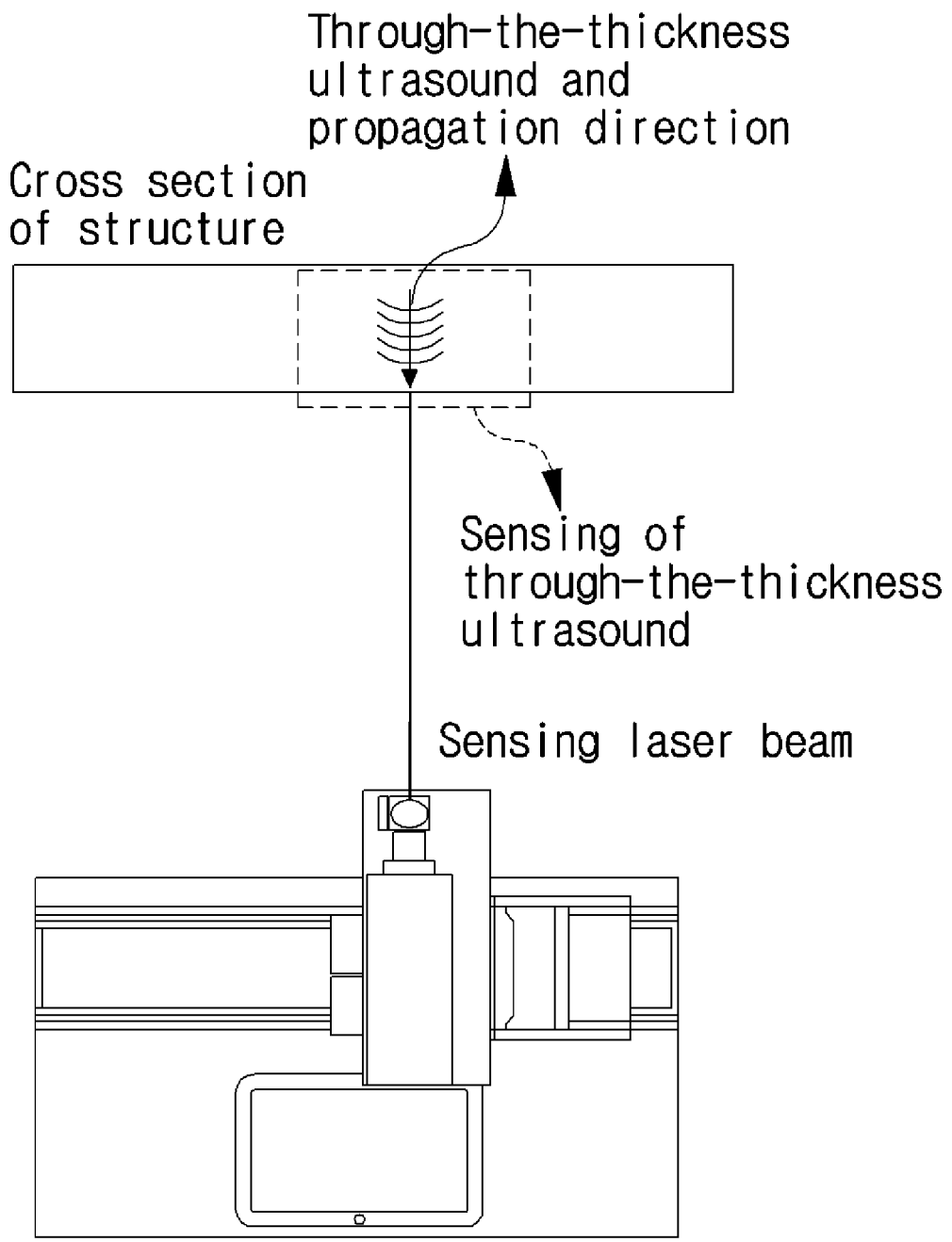

FIGS. 3A and 3B are a view showing a concept of collection in a through-the-thickness ultrasonic propagation mode. The full-field ultrasonic propagation imaging system according to an exemplary embodiment of the present disclosure generates a thermoelastic wave with abrupt thermal expansion at the same time of irradiating the surface of the structure with a laser beam pulse of a few to tens of nanoseconds generated in the ultrasound generation laser 110, and senses ultrasounds propagated through the thickness in various modes in real time through the ultrasound sensing laser 120.

The vertically linear stage 120 and the horizontally linear stage 140 are a two-axis linear stage system for moving two laser beams spacially, and scan the scan area on the surface of the structure with two laser beams simultaneously.

The vertically linear stage 130 and the horizontally linear stage 140 may be controlled by the linear stage system controller 190.

The inline band pass filter 170 filters the result of sensing by the ultrasound sensing laser 120.

The PC 180 is a kind of image generation device which receives a result of sensing by scanning the structure with the two laser beams and generating ultrasounds through the inline band pass filter 170, and generates an ultrasonic propagation image.

The ultrasonic propagation image generated by the PC 180 is an image which shows a process of propagating ultrasounds through the thickness of the structure with time. That is, the ultrasonic propagation image corresponds to a moving image or a still image in which the results of the sensing acquired through scanning are time-synchronized and arrayed. In addition, the through-the-thickness location of a defect or damage may be calculated based on a propagating time and a propagation speed. In addition, the PC 180 further signal-processes the result of the sensing in a frequency, wave number, or wavelength domain, and suggests the result of the sensing as a moving image or an image.

Figure 4:
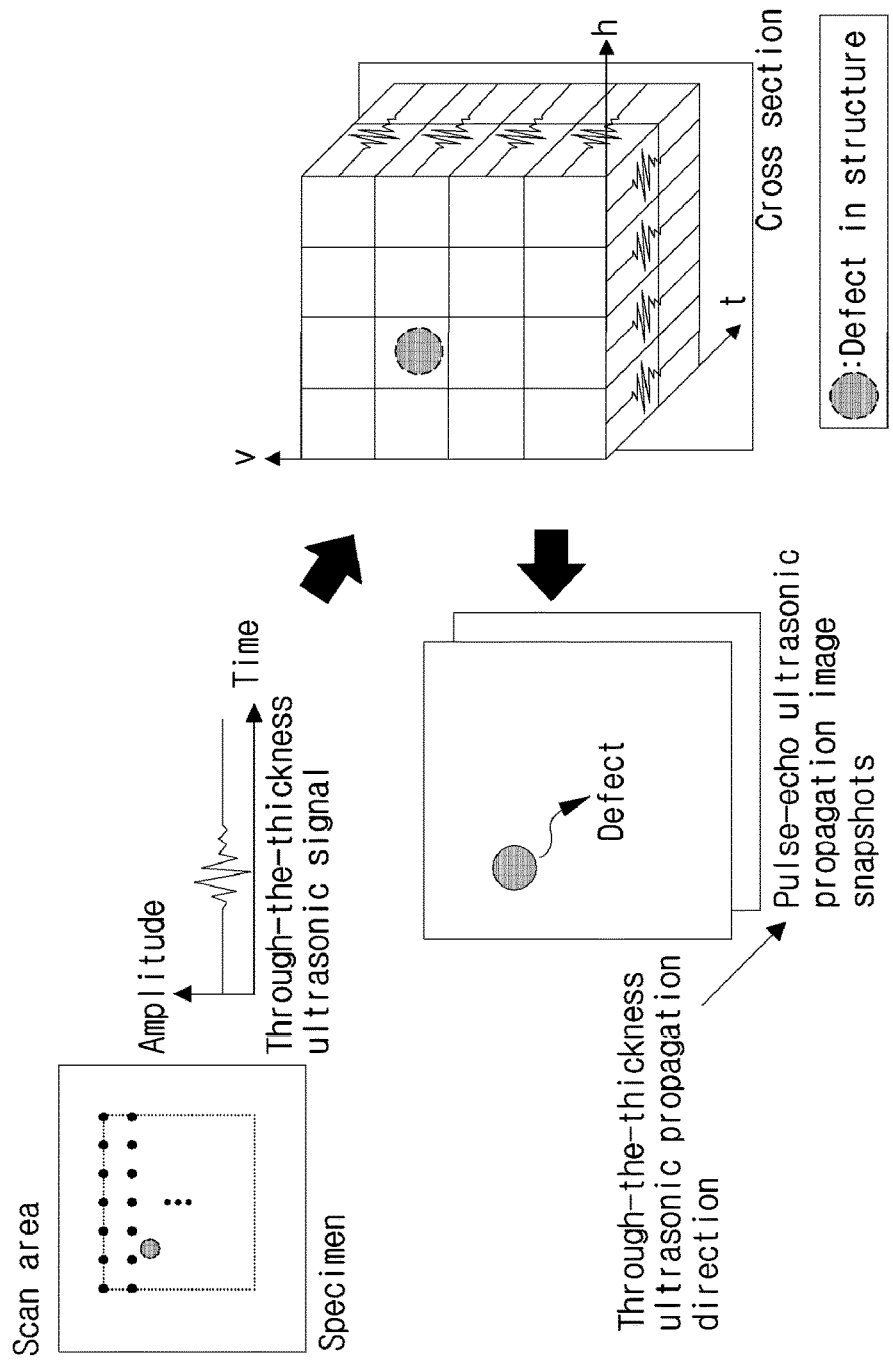
FIG. 4 is a view to illustrate a through-the-thickness ultrasound-based pulse-echo ultrasonic propagation imaging technique.

FIG. 4 is a view to illustrate a through-the-thickness ultrasound-based pulse-echo ultrasonic propagation imaging technique. As shown in FIG. 4, a defect in a specimen is visualized through the pulse-echo ultrasonic propagation imaging technique based on the through-the-thickness ultrasounds acquired from the specimen as a result of scanning. One-dimensional ultrasound signals which are collected by scanning are rearranged to a three-dimensional array, and generate an image along a time axis. When a moving image is made based on the signals, it can be visualized how uniform ultrasounds are propagated through the thickness over the full scan field.

Accordingly, the defect in the structure can be visualized by collecting laser-induced ultrasounds in the through-the-thickness propagation mode through a sensing laser, and then acquiring the full-field pulse-echo ultrasonic propagation image.

When the signal-to-noise ratio is determined to be less than or equal to a reference value by the PC 180, the controllers 161, 162, 190 control the ultrasound generation laser 110 and the ultrasound sensing laser 120 to scan the structure repeatedly.

The full-field pulse-echo laser ultrasonic propagation imaging system and method according to exemplary embodiments has been described up to now.

Figure 5:
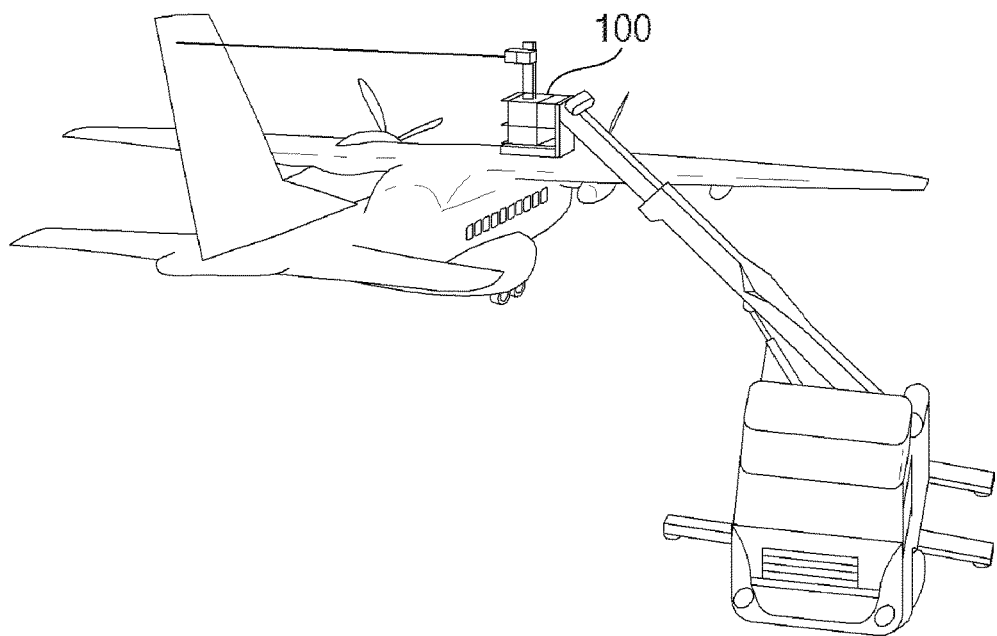
FIG. 5 is a view showing inspection of a vertical tail wing of a transport plane.
Figure 6:
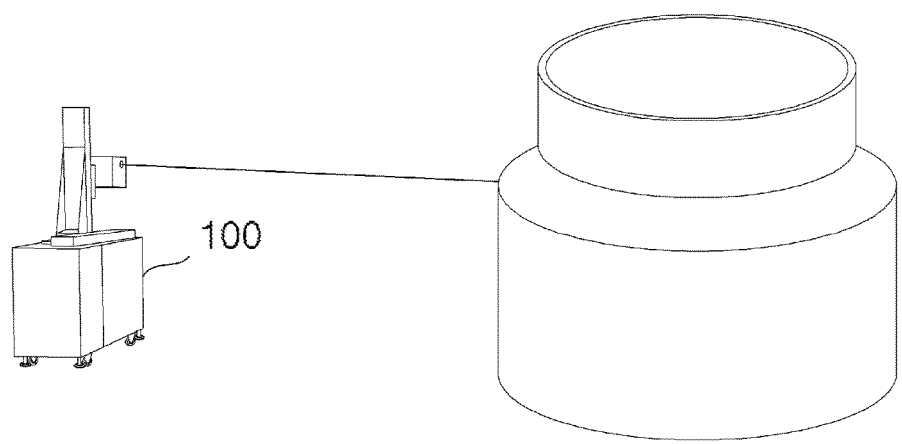
FIG. 6 is a view showing evaluation of quality of a Launching Vehicle structure.

The full-field ultrasonic propagation imaging system according to exemplary embodiments of the present disclosure may be applied to various fields. For example, the full-field ultrasonic propagation imaging system 100 may be used to inspect a vertical tail wing of a transport plane as shown in FIG. 5, and to evaluate quality of an launching vehicle structure as shown in FIG. 6, and may also be used for nondestructive testing of other structures.

Figure 7:
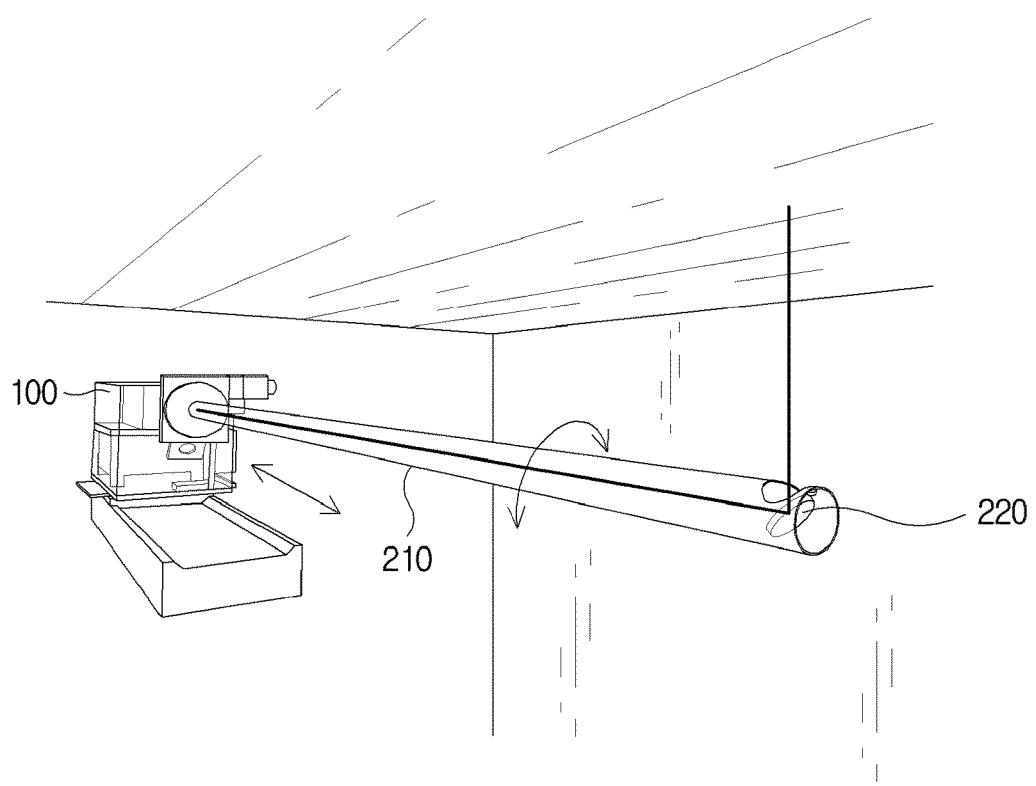
FIG. 7 is a view showing an exterior of a full-field pulse-echo laser ultrasonic propagation imaging system according to another exemplary embodiment of the present disclosure.

FIG. 7 is a view showing an exterior of a full-field ultrasonic propagation imaging system according to another exemplary embodiment of the present disclosure. The full-field pulse-echo laser ultrasonic propagation imaging system 100 illustrated in FIG. 7 may further include a laser guide 210 along which a source laser and a sensing laser travel. A mirror 220 installed at the rear end of the laser guide 210 is a means for changing the path of the laser, and is configured to scan the inner surface of the structure.

The full-field pulse-echo laser ultrasonic propagation imaging system 100 reciproates forward and backward and the laser guide 210 rotates in the directions of the arrows shown in FIG. 7 so as to scan the entire interior of the structure.

Although the present disclosure has been described with an exemplary embodiment, various changes and modifications may be suggested to one skilled in the art. It is intended that the present disclosure encompass such changes and modifications as fall within the scope of the appended claims.

What is claimed is:

1. A full-field ultrasonic propagation imaging system comprising:
   a generator configured to generate ultrasounds on a structure in a noncontact method by emitting first laser beams to a surface of the structure;
   a receiver configured to sense ultrasounds that are propagated in the structure in a thickness direction of the structure in a noncontact method by emitting second laser beams to the surface of the structure;
   a filter mirror and a reflection mirror, wherein the reflection mirror is configured to reflect the first laser beams generated by the generator to the filter mirror, and the filter mirror is configured to reflect the first laser beams reflected from the reflection mirror to the surface of the structure and pass the second laser beams emitted by the receiver therethrough and transmit the second laser beams to the surface of the structure;
   an image generating device configured to generate an ultrasonic propagation image based on the sensed ultrasounds;
   a horizontal linear stage extending in a horizontal direction;
   a vertical linear stage positioned on the horizontal linear stage and extending in a vertical direction, wherein the generator, the receiver, the filter mirror and the reflection mirror are attached to the vertical linear stage; and
   a linear stage system controller configured to control the vertical linear stage to move the generator, the receiver, the filter mirror and the reflection mirror attached to the vertical linear stage in the vertical direction and to control the horizontal linear stage to move the generator, the receiver, the filter mirror and the reflection mirror attached to the vertical linear stage in the horizontal direction,
   wherein the generator and the receiver are stacked together so that a beam axis of the generator is parallel with a beam axis of the receiver.

2. The full-field ultrasonic propagation imaging system of claim 1, wherein the ultrasonic propagation image is an image which shows a process of propagating the ultrasounds in the structure in the thickness direction of the structure with time.

3. The full-field ultrasonic propagation imaging system of claim 2, wherein the ultrasonic propagation image is a moving image or an image in which results of sensing acquired through scanning are arrayed in a time, frequency, wave number, and wavelength domains.

4. The full-field ultrasonic propagation imaging system of claim 1, further comprising a controller configured to, when a signal-to-noise ratio is less than or equal to a reference, control the generator and the receiver to scan the structure repeatedly.

5. The full-field ultrasonic propagation imaging system of claim 1, wherein the generator is configured to emit Q-switched laser beams and generate ultrasounds on the structure in the noncontact method.

6. The full-field ultrasonic propagation imaging system of claim 1, wherein the receiver is a continuous wave laser interferometer configured to sense the ultrasounds propagated in the thickness direction of the structure.

7. An ultrasonic propagation imaging method using a full-field ultrasonic propagation imaging system including a generator, a receiver, an image generating device, a horizontal linear stage extending in a horizontal direction, a vertical linear stage positioned on the horizontal linear stage and extending in a vertical direction, and a linear stage system controller, the method comprising:
   generating, by the generator, ultrasounds on a structure by emitting first laser beams to a surface of the structure;
   sensing, by the receiver, ultrasounds that are propagated in the structure in a thickness direction of the structure by emitting second laser beams to the surface of the structure; and
   generating, by the image generating device, an ultrasonic propagation image based on the sensed ultrasounds,
   wherein the first laser beams emitted by the generator are reflected by a reflection mirror to a filter mirror and then are reflected by the filter mirror to the surface of the structure, and the second laser beams generated by the receiver pass through the filter mirror and are transmitted to the surface of the structure,
   wherein the generator, the receiver, the filter mirror and the reflection mirror are attached to the vertical linear stage,
   wherein the method further comprises controlling, by the linear stage system controller, the vertical linear stage to move the generator, the receiver, the filter mirror and the reflection mirror attached to the vertical linear stage in the vertical direction, and controlling, by the linear stage system controller, the horizontal linear stage to move the generator the receiver, the filter mirror and the reflection mirror attached to the vertical linear stage in the horizontal direction, and
   wherein the generator and the receiver are stacked together so that a beam axis of the generator is parallel with a beam axis of the receiver.

* * * * *